United States Patent [19]

Drewlow

[11] Patent Number: Plant 6,928

[45] Date of Patent: Jul. 18, 1989

[54] BEGONIA PLANT NAMED LANCELOT

[75] Inventor: Lyndon W. Drewlow, Ashtabula, Ohio

[73] Assignee: Mikkelsens Inc., Ashtabula, Ohio

[21] Appl. No.: 195,284

[22] Filed: May 18, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Begonia plant named Lancelot having large, fully double intense scarlet red flowers, vigorous and upright growth habit, thick and strong main stems which hold the flowers upright, and year around flowering without four week short day treatment.

1 Drawing Sheet

The present invention relates to a new and distinctive cultivar of Begonia plant, botanically known as *Begonia hiemalis* Fotsch, and known by the cultivar name Lancelot.

The new cultivar was discovered by the inventor Lyndon W. Drewlow as a seedling resulting from a controlled crossing by the inventor of Mikkelsen Seedling No. 84-648-4 as the seed parent with Mikkelsen Seedling 85-1041-1 as the pollen parent.

Asexual reproduction by stem and/or leaf cuttings by the inventor has established that the unique features of the new cultivar are reproduced through successive propagations.

The following characteristics distinguish Lancelot from both its parents and other Begonias commercially known and used in the floriculture industry, with the described characteristics in certain instances being compared with commercially well known and patented cultivars.

1. Lancelot has intense scarlet red flowers which are similar in color to Hilda (U.S. Plant Pat. No. 5,532). Dorthe (U.S. Plant Pat. No. 5,162) has light scarlet flowers, and both Fresco (U.S. Plant Pat. No. 4,781) and Schwabenland Red (U.S. Plant Pat. No. 3,317) are orange-red in color.
2. Lancelot has larger flowers than any of the four comparison cultivars.
3. Lancelot has full double flowers similar in doubleness to Hilda and Dorthe. Schwabenland Red is a single flowered cultivar while Fresco is semi-double.
4. Lancelot is an upright growing cultivar similar to Schwabenland Red in height and plant shape. Fresco and Hilda are more compact and a little more dense in habit. Dorthe is more mounded making a trailing hanging basket.
5. Leaf color of Lancelot is green with a slight red margin on young leaves. Schwabenland Red has green leaves, Fresco purplish red leaves, and Hilda and Dorthe have reddish green leaves.
6. Lancelot and Schwabenland Red have green main stems, compared with the main stems of Hilda which are reddish green, and Dorthe and Fresco which are purplish-red.
7. Lancelot and Schwabenland Red have a reddish cast to the main flower peduncle, while Hilda has a red peduncle; Fresco and Dorthe have reddish purple peduncles.

8. Leaf size of Lancelot is similar to Schwabenland Red and Fresco, but larger than Hilda and Dorthe. Also, the leaves of Lancelot are slightly thicker, and have a more leathery feeling than the leaves of all four comparison cultivars.
9. The leaves of Lancelot, Hilda, and Fresco have pointed tips, while the leaves of Dorthe and Schwabenland Red have more rounded tips. The leaf margin of Lancelot is less serrated than Fresco, similar to Hilda and more serrated than Dorthe and Schwabenland Red.
10. Flowering will occur year around without a four (4) week short day treatment. However, short treatment will increase the number of flowers per plant.
11. Distinct scarlet flowers that are rose shaped and fully double.
12. Thick strong stems hold the large flowers without breaking over.
13. Upright habit makes Lancelot ideal for 15, 20 and 25 cm pots.

The accompanying colored photograph illustrates in perspective view the overall appearance of Lancelot, with colors being as true as it is reasonably possible to obtain in a colored reproduction of this type.

The following is a detailed description of my new Begonia cultivar based on plants produced under commercial practices in Ashtabula, Ohio, under greenhouse conditions. The photograph was taken in early August, 1987. Color references are made to The Royal Horticultural Society Colour Chart except where general color terms of ordinary dictionary significance are used.

Parentage: Controlled cross between female parent Mikkelsen Seedling No. 84-648-4 and male parent Mikkelsen Seedling No. 85-1041-1.

Propagation:

(A) *Type cutting.*—Leaf and stem cuttings.

(B) *Time to root (leaf cutting).*—18 days at 21° C. summer; 24 days at 21° C. winter.

*Time to root (stem cutting).*—14 days at 21° C. summer; 21 days at 21° winter.

(C) *Rooting habit.*—Abundant, fine, fibrous for both leaf and stem rootings.

(D) *Time for shoot development.*—From leaf cuttings, 10 weeks in summer to 13 weeks in winter to obtain shoots 4 to 5 cm long in length; from stem cuttings, salable shoots of similar size are obtained in five (5) weeks.

Plant description:

(A) *Form.*—Upright, excellent stem strength for self-support, tall, intermediate internodes. Suitable for 15, 20 and 25 cm pots.

(B) *Habit of growth.*—Vigorous, fast upright growth with some basal branching from an unpinched stem cutting and excellent basal branching from a pinch. Usually vegetative shoots are formed at basal nodes and flower shoots at the higher nodes.

(C) *Foliage.*—Leaves simple, alternate, borne on strong petioles 6–7 mm in diameter on mature leaves. (1) Size: Can vary greatly with leaf position on plant, number of leaves per plant, and environment. Approximately 80 to 100 mm across when mature. (2) Shape: Cordate but lobes overlap at stem attachment point. (3) Texture: Leathery, glabrous. (4) Margin: Serrated. (5) Color: Young foliage, top side 146B, with red tinge at margins; under side 146C, with red tinge at margins. Mature foliage, top side 147A; under side 148B. (6) Venation: Palmate with 5 major veins.

Flowering description:

(A) *Flowering habits.*—Flowering in racemes, 2 or 3 per raceme, with several racemes in bloom at one time; flowering continues more or less indefinitely.

(B) *Flowering season.*—Will flower year around without controlling daylength. Plants will flower more abundantly if subjected to a reduced daylength of 12 hours for 4 weeks when plants are actively growing in final pot size.

(C) *Flower buds.*—Approximately 20 mm long and 25 mm wide just before opening; tepals are entire around margins; color 46B just before opening and 45A when immature.

(D) *Flowers borne.*—On strong upright peduncles reddish green in color and approximately 5 mm in diameter.

(E) *Quantity.*—Average of 3 per peduncle, opening in sequence as raceme develops. Number of flowers will vary with number of flowering shoots per plant.

(F) *Tepals.*—(1) Shape: Outer ones nearly rounded, inner heart-shaped. (2) Color top side in summer when opening: 46B, fading to 45B; underside 45C. (3) Number of tepals: 20 to 25 or more. (4) Size of tepals: Outer tepals 35 mm in diameter, inner tepals approximately 25 mm. (5) Flower size: 60–70 mm in diameter.

(G) *Reproductive organs.*—(1) Stamens: None as plant is fully double with anthers appearing as petals. (2) Pistils: (a) Stigma shape: Curled, color reddish-orange. (b) Style color: Scarlet. (c) Ovaries: Three in number, one 10 to 15 mm long wing and two 5 to 10 mm long wings, 10 mm in diameter, reddish green in color.

Disease resistance: Lancelot has shown good disease resistance to powdery mildew.

I claim:

1. A new and distinct cultivar of Begonia plant named Lancelot, as illustrated and described, and parts thereof.

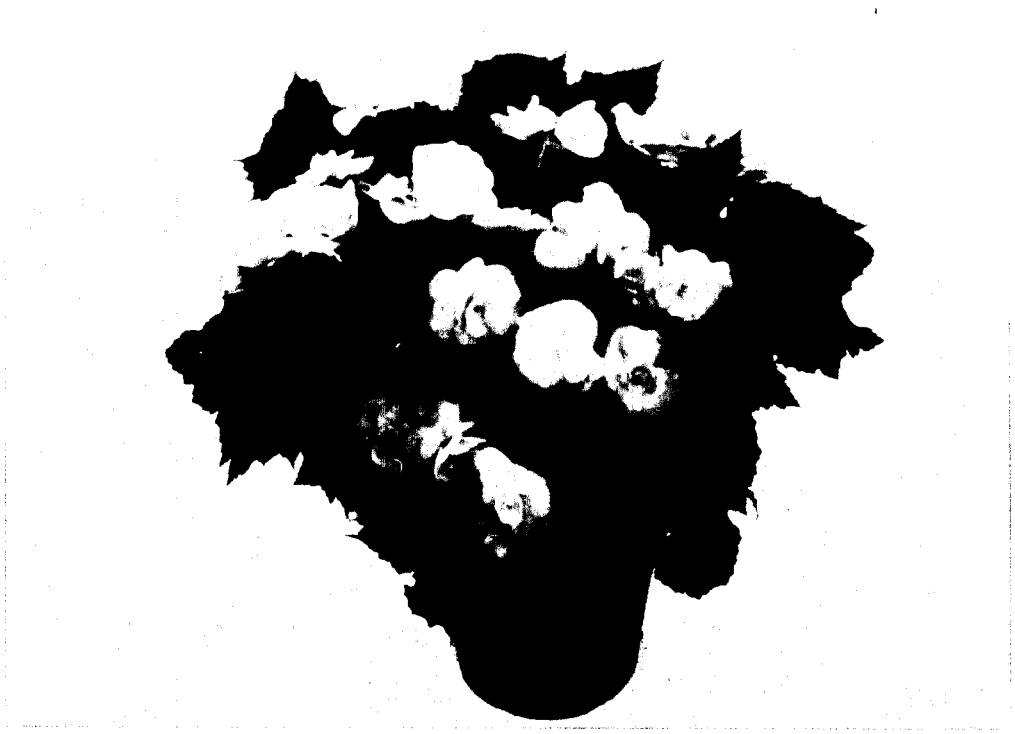

* * * * *